United States Patent [19]
Halliday et al.

[11] Patent Number: 5,939,046
[45] Date of Patent: Aug. 17, 1999

[54] METHOD OF EVALUATING AN EFFECT OF A SUBSTANCE APPLIED TO THE SKIN OF A MAMMAL

[76] Inventors: Gary M. Halliday, 176 Denison Street, Newtown New South Wales 2042; Diona L. Damian, 9 Udall Avenue, Five Dock New South Wales 2046; Ross St. C. Barnetson, 8 Narena Close, Beecroft New South Wales 2119, all of Australia

[21] Appl. No.: 08/983,387

[22] PCT Filed: May 16, 1997

[86] PCT No.: PCT/AU97/00300

§ 371 Date: Mar. 17, 1998

§ 102(e) Date: Mar. 17, 1998

[87] PCT Pub. No.: WO97/44066

PCT Pub. Date: Nov. 27, 1997

[30] Foreign Application Priority Data

May 17, 1996 [AU] Australia ...................................... 9916
Sep. 4, 1996 [AU] Australia .................................. 02138

[51] Int. Cl.$^6$ ..................................................... A61K 49/00
[52] U.S. Cl. ............................................................ 424/9.81
[58] Field of Search ............................................. 424/9.81

[56] References Cited

U.S. PATENT DOCUMENTS 5,302,389  4/1994  Kripke et al. .......................... 424/94.6

OTHER PUBLICATIONS

Bestak et al, *Jour. Invest. Dermatol.*, 105, 345–351, 1995.
Hersey et al, *Jour. Invest. Dermatol.*, 88, 271–276, 1987.
Reeve et al, *Jour. Invest. Dermatol.*, 97, 624–628, 1991.
Roberts et al, *Jour. Invest. Dermatol.*, 105, 339–344, 1995.
Whitmore et al, *Arch. Dermatol.*, 131, 1128–1133, 1995.
Wolf et al, Jour. Invest Dermatol., 100, 254–259, 1993.

*Primary Examiner*—David Saunders
*Attorney, Agent, or Firm*—Welsh & Katz, Ltd.

[57] ABSTRACT

A method for evaluating an effect of a substance when applied to mammalian skin is provided. The method comprises the steps of: (i) assessing an immune response of the skin of at least one mammal to an antigen, to which the mammal has been sensitized, in order to obtain data; (ii) applying the substance to the skin; (iii) assessing the immune response of the skin to the antigen following the application of the substance to the skin to obtain further data; and (iv) using the data obtained in steps (i) and (iii) to evaluate the effect of the substance.

14 Claims, 1 Drawing Sheet

METHOD OF EVALUATING AN EFFECT OF A SUBSTANCE APPLIED TO THE SKIN OF A MAMMAL

TECHNICAL FIELD

The present invention relates to a method for evaluating an effect of a substance on the immune response of the skin of a mammal. The method may be used to provide information which can be shown on commercial preparations of substances so that consumers are better able to make a comparison between such substances. The invention also relates to the substance evaluated by the method.

BACKGROUND ART

Exposure to UV radiation can cause erythema (sunburn), the formation of DNX pyrimidine dimers, premature ageing and dermal connective tissue changes. It is common to evaluate the protection from erythema provided by a sunscreen preparation by determining its sunscreen protection factor (SPF). The practice, of determining SPF is useful not only in providing information as to the effectiveness of different sunscreen preparations in protecting against erythema, but also in the determination of a minimum level of protection which must be met before a given sunscreen preparation can be marketed commercially.

Studies have shown that exposure to ultraviolet radiation can also profoundly impair the cutaneous immunity of mammals and it is widely believed that ultraviolet radiation induced immunosuppression contributes significantly to cutaneous carcinogenesis.

The effects of UV radiation on the immune system include reduced contact hypersensitivity (CHS) and delayed hypersensitivity reactions, systemic immunosuppression in mice, and tolerance of tumours in mice or epicutaneous antigens in humans [Noonan 1981, Hersey 1983, Ullrich 1986, Cestari 1995, Cooper 1992]. In humans, such alterations in immunity can occur even with small, suberythemal doses of UV.

Where cutaneous immunity is markedly affected by long-term, systemic immunosuppressive medications, as is seen in transplant recipients, the incidence of non-melanoma skin cancer is ten to one hundred-fold higher than in age-matched, immunologically competent controls [London 1995, Espana 1995].

It is, therefore, important that human beings who are exposed to even small doses of UV radiation be protected not only from the erythemal and mutagenic effects of sunlight, but also from its immunosuppressive effects. While sunscreens can decrease the formation of pyrimidine DNA dimers [Freeman 1988], reduce the incidence of pre-malignant solar keratoses [Thompson 1993, Naylor 1995], can delay and even prevent UV tumorigenesis in mice [Kligman 1980], and may help reduce the incidence of skin cancer in humans, if they fail to protect the immune system then individuals using high SPF sunscreens who tend to stay in the sun for extended periods may become severely immunosuppressed and have an increased risk of skin malignancy.

Recently, Whitmore et al [1995] found that a high SPF sunscreen completely prevented UV suppression of induction of primary contact sensitisation to dinitrochloroberizene (DNCB). Work in mice suggests that UV immunoprotection is more dependent on broad spectrum cover than SPF [Bestak 1995], since the erythemal and immunosuppressive spectra are probably different.

Previous studies of UV suppression of CHS have used induction of primary CHS to antigens such as DNCB. However, since induction of primary CHS requires exposure to an antigen for the first time the immune response to the antigen cannot be anticipated and it is possible the exposure may elicit a severe response which is, of course, undesirable.

Induction of primary CHS to an antigen also necessarily means that the resultant immune response may only be evaluated once in a given subject. Accordingly, in order to evaluate the ability of a substance to suppress a skin immune response or to evaluate the protection provided by the substance against suppression of the immune response by ultraviolet radiation using induction of primary CHS, a large number of different individuals are required. This is also undesirable and is compounded by the need to use different groups of individuals each time a substance is evaluated.

With the increasing availability of high SPF sunscreens, such as SPF 30, which encourages individuals to stay in the sun for substantial periods of time, there is a need for a reliable and relatively convenient method for evaluating the amount of immunoprotection afforded by commonly used sunscreen ingredients and sunscreens in general. Similarly, there is a need for a suitable and effective method for evaluating whether the cutaneous immunity of an individual is impaired by a substance when applied to the individual's skin.

DISCLOSURE OF INVENTION

In a first aspect of the present invention there is provided a method of evaluating an effect of a substance when applied to mammalian skin, comprising the steps of:

(i) assessing an immune response of the skin of at least one mammal to an antigen, to which the mammal has been sensitised, in order to obtain data;

(ii) applying the substance to the skin;

(iii) assessing the immune response of the skin to the antigen following the application of the substance to obtain further data; and (iv) using the data obtained in steps (i) and (iii) to determine information to evaluate the effect of the substance.

In a second aspect of the invention there is provided the substance evaluated by the method.

In a third aspect of the invention there is a method of providing a product comprising an evaluated substance for topical application to mammalian skin, involving:

(a) evaluating the substance with the use of information obtained by the steps of:

(i) assessing an immune response of the skin of at least one mammal to an antigen, to which the mammal has been sensitised, to obtain data;

(ii) applying the substance to the skin;

(iii) assessing the immune response of the skin to the antigen following the application of the substance to obtain further data; and (iv) using the data obtained in steps (i) and (iii) to determine the information.

Typically, the product will consist of a container such as a jar, bottle, vial, tube or sachet containing the evaluated substance. The product may also comprise packaging that holds or displays the container. Any conventionally known packaging may be used for this purpose.

If desired, the information can be provided so that the result of the evaluation is shown with the product. Indeed, the information can be marked directly on the container or packaging, or for instance, be provided by means of a label, tag or the like attached to the container or packaging.

The evaluating may comprise determining whether the substance suppresses or enhances the immune response of the skin to the antigen and the level of suppression or enhancement of the immune response resulting from the contact of the skin with the substance.

Alternatively, the evaluating may comprise determining whether the substance protects the immune response of the skin to the antigen from ultraviolet radiation. In this instance, the method can be used to measure the protection provided by the substance to the immune response of the skin from the ultraviolet radiation. In order to determine or measure such protection the skin is exposed to ultraviolet radiation in the presence of the substance.

The skin may also be exposed to ultraviolet radiation prior to the application of the substance. Usually, the minimum dose of ultraviolet radiation which suppresses the immune response of the skin in the absence of the substance and the minimum dose of ultraviolet radiation given to the skin in the presence of the substance which suppresses the immune response will be determined.

This data can be used to calculate an immune protection factor (IPF) for the substance. However, if desired, other data provided by the method may be used to calculate the IPF. Similarly, data obtained while carrying out the method can be used to calculate an immune suppression factor (ISF) or immune enhancement factor (IEF) in those instances where the substance is known or found to suppress or enhance the cutaneous immunity of the skin.

By evaluating such effects the commercial worth of the substance may be enhanced since consumers will generally prefer substances which have been shown to have limited deleterious effects, or which have been shown to have a desired characteristic or a desired level of such characteristic (e.g., a desired IPF value).

The antigen can be a metal, a polypeptide such as purified protein derivative of tuberculin, or other material. Preferably, the metal is nickel or chrome. Most preferably, the antigen is nickel.

In order to evaluate the immune responses of the skin the antigen may be applied to the surface of the skin or be injected into the skin. Preferably, patches containing a predetermined dose of the antigen are used to apply the antigen.

Typically, the mammalian skin will be the skin of one or more human beings. Since the mammal or mammals have previously been sensitised to the antigen it will be understood that the antigen is a recall antigen.

By using a recall antigen a mammal can be exposed to the antigen any number of times and a consistent immune response obtained on each challenge for a given amount of the antigen. Suppression of the immune response to the antigen or protection against ultraviolet radiation provided to the immune response by different substances can also be evaluated on one mammal at the some time. In addition, the method can be used on the same mammal on different occasions. This is particularly advantageous when the mammal is a human being as it avoids the necessity to recruit new people each time a substance is to be evaluated using the method.

Furthermore, the method allows preliminary testing of the immune response to the antigen so that those with a desired level of response can be selected for studies using the method of the invention, and those having low or high responses can be excluded. Moreover, the undesirable use of potentially carcinogenic compounds such as DNCB on people and ethical problems associated with such use can be avoided.

MODES FOR CARRYING OUT THE INVENTION

Figure 1:
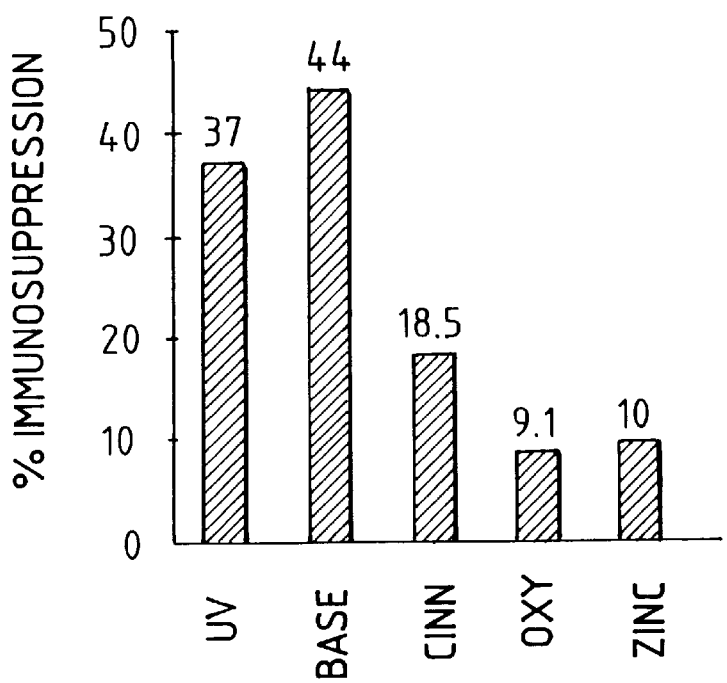
FIG. 1 illustrates the immunosuppression in unprotected human skin following exposure to UV radiation compared to skin protected by different sunscreen lotions. The immune response was evaluated using an erythema spectrometer.

Substances that may be evaluated with the use of the method include sunscreen, cosmetic and pharmaceutical preparations. The preparations may be in the form of, for instance, a lotion, cream, gel or ointment. It will further be appreciated that an ingredient or combination of ingredients for possible use in providing such preparations may also be evaluated by the method. In this instance, the ingredient or ingredients can be mixed with a carrier for the purpose of assisting in applying the substance to the skin at a desired concentration, wherein the carrier has only a minor or negligent effect on the immune response of the skin to the antigen.

A sample taken from a batch of the substance or alternatively, a sample obtained or prepared separately from the batch to be evaluated can be used in the method. Once evaluated, the batch of the substance can be utilised in the preparation of products marked with or otherwise showing the result of the evaluation for sale or distribution to consumers.

1.0 EXPERIMENTAL

To evaluate the use of a recall antigen in determining the protection provided by a sunscreen against the immunosuppressive effect of UV radiation nickel was selected as it is the most common contact antigen to which the general population has been sensitised. It has been reported that up to 10% of women [Peltonen L, 1979] and 4% of men [Meijer, 1995] develop allergic contact dermatitis when exposed to nickel, most commonly in response to contact with earrings, watchbands and other jewellery.

For the study, people with symptoms suggestive of nickel allergy were recruited from the general population The individuals were otherwise immunologically normal, and had not experienced sun exposure of their backs in the four weeks preceding the study. Nickel allergy was confirmed in each individual by patch testing with various concentrations of nickel sulphate.

1.1 PATCH TESTING

To confirm nickel allergy a number of preparations containing nickel sulphate in a petrolatum base (Trolab Herman, Germany) were placed in 9 mm diameter Finn chambers, and the patches taped to the mid to upper back. Each volunteer was initially patch tested with 5 concentrations of nickel (0.125%, 0.25%, 0.5%, 1% and 2.5%) in order to determine which concentration elicited the minimum reaction needed for the study in each volunteer. In this way, more severe, vesicular reactions were able to be avoided during subsequent patch testing.

The patches were removed after 48 hours and the response assessed 30 minutes later and then 24 hours later by means of a clinical scoring system (see Table 1). A positive nickel reaction consisted of erythema with induration at the site of the patch test. Only volunteers who proved allergic to nickel and displayed a confluent nickel reaction (score of 3 or more), were used in the study.

TABLE 1

Clinical Scoring System for Assessing Nickel CHS Reactions

| SCORE | OBSERVATION |
|---|---|
| 0 | No reaction |
| 1 | Isolated vesicles/pustules |
| 2 | Limited, non-confluent induration. No vesicles |
| 3 | Mild, confluent induration. No vesicles |
| 4 | Moderate, confluent induration. No vesicles |
| 5 | Vesicles over <25% of the patch area |
| 6 | Vesicles over 25–50% of the patch area |
| 7 | Vesicles over 50–75% of the patch area |
| 8 | Vesicles covering the entire patch area |
| 9 | Vesicular reaction spreading beyond the patch area |
| 10 | Bullous reaction |

1.2 SUNSCREENS

Three different sunscreen lotions and an oil-in-water base lotion common to each sunscreen were used in the study. The three sunscreens contained 5% cinnamate, 3.5% cinnamate with 2.0% oxy benzone, and 3.0% cinnamate with 2.05% zinc oxide, respectively.

1.3 DETERMINATION OF THE SUN PROTECTION FACTOR (SPF) OF THE SUNSCREENS

The SPF of each sunscreen and the base lotion was determined in vivo on the backs of 5 human volunteers. The UV source was the same fluorescent lamp array used in the irradiation protocol described below, and the lotions were applied at a concentration of 2 mg/cm$^2$, 15 minutes prior to irradiation. The area of skin to be irradiated was divided into segments, to assist in the application of the three different sunscreens and their base lotion to different areas of the volunteers' skin. All lotions were removed with soap and water at the completion of the irradiation. The total contact time of each sunscreen was less then 25 minutes.

The minimum erythemal dose (MED) was determined as the minimum dose at which clearly demarcated erythema was observed, and the SPF was calculated as the ratio of the MEDs of sunscreen-treated and unprotected skin. The cinnamate only and cinnamate+oxybenzone lotions had an average SPF of 10, while the cinnamate+zinc oxide lotion was SPF 9.5 and the base lotion SPF 1.

1.4 IRRADIATION

To assess the effect of UV radiation on the immune response to nickel a UV source comprising an alternating array of 2 UVB (20W Philips TL12) and 6 UVA (20W NEC T10) fluorescent lamps was used. The lamps were filtered with 0.5 mm cellulose triacetate film (Eastman Kodak, Rochester, N.Y.), to remove any UVC (<290 nm) and to attenuate the lower wavelength UVB emission so that the spectrum more closely approximated sunlight. The integrated irradiance of the lamps at the skin surface was 0.3245 mW/cm$^2$ UV3 and 4 mMW/cm$^2$ UVA, determined daily with an IL1350 broadband radiometer using SED 038 (UVA) and SED 240 (UVB) detectors calibrated against the source (CSIRO, Sydney, Australia).

Using this apparatus, the minimum erythemal dose (MED) of the skin of the mid to upper back was determined for each nickel sensitive subject as the lowest dose of UVB at which clearly demarcated erythema was seen.

The skin of the mid-back was then irradiated through a 4 cm×6 cm template with a suberythemal dose of UVB (97.5±2.5 mJ/cm$^2$) and accompanying UVA (1.23 J/cm$^2$) radiation daily for 5 consecutive days. All individuals (numbering 16) received the same amount of UV radiation regardless of skin type and different 2 cu$^2$ areas of the template were selected in each individual for the daily application of each respective sunscreen and base lotion prior to irradiation.

After the fifth and final irradiation, the nickel patches were applied to the back: one patch was placed in each of the four segments used to test the sunscreens and base lotion, one patch tested unprotected irradiated skin, and two control patches were placed on adjacent, unirradiated skin with and without sunscreens. The patches were left in place for 48 hours, and the CHS response elicited was assessed both clinically and with a reflectance spectrometer (Diastron, UK) 24 hours after their removal.

All readings with the reflectance spectrometer were taken in triplicate with subjects resting in the prone position, and an average reading calculated for each site. There was reasonable correlation between clinical scoring of the nickel reactions and objective assessment using the erythema spectrometer.

None of the individuals who participated in the study suffered significant adverse effects from the nickel patch testing, and all of the eligible volunteers completed the study. However, several individuals were excluded from the results because of insufficient nickel reaction at the unirradiated control site (i.e., due to a score of less than 3, meaning lack of confluent induration), despite a previously strong reaction to the initial patch test.

1.5 EVALUATION OF PROTECTION AGAINST IMMUNE RESPONSE SUPPRESSION BY UV RADIATION

An erythema index (EI) was calculated as the difference between the erythema reading at the nickel test site and the erythema reading of adjacent skin. UV immunosuppression was deterred by comparing the nickel induced EI at irradiated test sites to unirradiated test sites.

Figure 2:
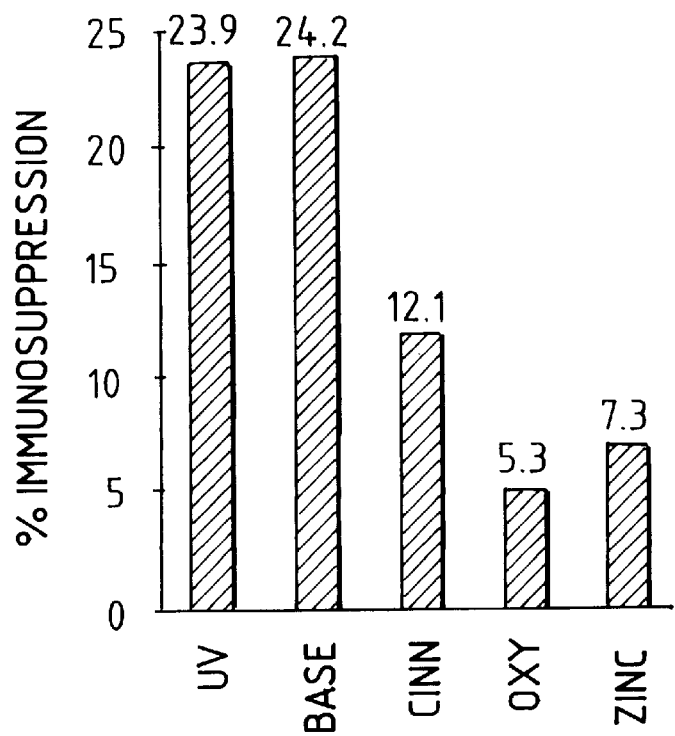
FIG. 2 shows the results when a clinical scoring method was used to evaluate the immune response instead of the erythema spectrometer.

Immunosuppression in unprotected, irradiated skin was not found to vary with either age or MED. When the nickel reactions of unprotected, irradiated skin were compared with those of unirradiated skin there was, on average, immunosuppression of 37% as determined using the erythema meter and 25% using clinical scores as shown in FIGS. 1 and 2 respectively. In almost all cases, this attenuation of the nickel reaction was clearly visible and palpable.

The figures also show that the application of the cinnamate only sunscreen did not prevent significant immunosuppression from occurring since 18.5% immunosuppression was determined using the erythema spectrometer while 12.1% immunosuppression was observed using clinical scores. In contrast, the sunscreen containing both cinnamate and oxybenzone protected against significant immunosuppression. In this instance, there was only a 9.1% reduction in the mean erythema index and a 5.3% reduction in the mean clinical score of sites irradiated after application of the sunscreen. The sunscreen containing cinnamate and zinc oxide also prevented significant immunosuppression as indicated by a 10.0% reduction in the mean erythema index and a 7.3% reduction in the mean clinical score. Application of the base lotion prior to irradiation had no effect on either the erythema index or the clinical score.

Each of the three sunscreens and their base lotion was also tested for any effect in the absence of UV. None of the lotions had a significant effect on the nickel CHS reaction in the absence of UV.

The results show that nickel patch testing is a clinically feasible means of quantitatively assessing UV immunosuppression in human subjects. The results also show that significant UV immunosuppression of the nickel CHS response can be induced in humans with a low dose 5-day UV protocol, and that even with low doses of UV radiation, immunosuppression is not completely prevented by a relatively high SPF but narrow spectrum sunscreen (cinnamate).

Rather than inducing primary allergic sensitisation in human subjects, the above model uses CHS to a recall antigen. Individuals can therefore be tested on more than one occasion and each individual can be used to test several sunscreens. Recent studies of the reproducibility of nickel patch testing suggest that nickel patch testing on the back gives highly reproducible results both clinically and with an erythema meter in up to 95% of tests [Memon 1996].

EXAMPLE 1

The use of a recall antigen to determine the level of protection against UV radiation able to be provided to the immune system of a human being by a sunscreen is described below.

Different 1 $cm^2$ areas of the skin of the upper back of an individual were irradiated with either 0, 50, 70, 90, 110, 130, 150 or 170 $mJ/cm^2$ UVB radiation using the UV source described above. Accordingly, the UVB dosages were accompanied by a UVA radiation component which increased substantially proportionately with each UVB dosage. The different areas were selected using a template laid over the individual's back.

So that at least one of the doses of UVB radiation caused immunosuppression in the skin of the individual the different areas were irradiated on five consecutive days at intervals of about one day for a period sufficient for each respective area to receive its allocated UV radiation dosage. Each respective area received substantially the same dosage on each exposure to the UV source.

After the final irradiation nickel patches, dosed with the sate amount of 0.5% nickel sulphate, were positioned on each area of the skin for a period of 48 hours. The contact hypersensitivity response elicited by the nickel was then assessed clinically 24 hours after the removal of the patches as described above.

The minimum immunosuppressive dose (MID) of UVB found to suppress the immune response was 70 $mJ/cm^2$ UVB.

A 2 $mg/cm^2$ amount of the sunscreen was then applied to different 1 $cm^2$ areas of the skin of the upper back of the individual 15 minutes prior to irradiation with a multiple of the MID determined above, namely 70, 140, 210 or 280 $mJ/cm^2$ UVB and using the same UV source.

A further 1 $cm^2$ area of the skin of the upper back was irradiated with 70 $mJ/cm^2$ UVB and accompanying UVA but in the absence of the sunscreen as a negative control. For the positive control another area of the skin to which the sunscreen was not applied and which was not irradiated was used.

Subsequently, the sunscreens were removed from the skin by washing with soap and water, and each area of the skin was patch tested with nickel using the same protocol when determining the MID, and the immune response to the nickel again measured 24 hours after the removal of the patches.

The minimum dose of UVB radiation which caused suppression of the immune response in the presence of the sunscreen was then determined.

The suppression of the immune response to the nickel was evaluated by firstly determining the difference in the immune response between the positive control and the negative control to provide a negative control erythema index (EI). The difference in the immune response between each area irradiated to that obtained for the positive control was then determined to provide a test erythema index for each area. So significant difference between a test erythema index and the negative control erythema index indicated that the immune response to the nickel had been suppressed by the corresponding dosage of UVB radiation, whereas a significantly lower test erythema index compared to the negative control erythema index indicated that suppression of the immune response had not occurred at that UVB radiation dosage.

In the present example, the immune response of the area of the skin irradiated with 210 $mJ/cm^2$ UVB was substantially the same as that observed for the area of the skin used as the positive control. Accordingly, no suppression of the immune response was observed at this dosage of UVB radiation. However, the immune response of the area of the skin irradiated with 280 $mJ/cm^2$ UVB and that obtained for the negative control was substantially the same indicating that suppression of the immune response had occurred.

Hence, the minimum dose of UVB radiation which caused suppression of the immune response to the nickel in the presence of the substance was 280 $mJ/cm^2$. The immune protection factors (IPF) of the sunscreen could then be calculated by dividing this value by the MID. Using this method, the IPF of the sunscreen is 280/70 which equals 4.

The IPF, therefore, is a measure of the protection provided to the individual by the sunscreen against suppression of the individual's immune response by exposure to UVB radiation. Accordingly, a sunscreen with a higher IPF would provide greater protection against suppression of the immune response than provided by the sunscreen used in the present example.

If desired, the IPF may be calculated in other ways, such as by subtracting the MID from the minimum dose of UV radiation which caused depression of the immune response in the presence of the substance. In this instance, the IPF would be 280–70 which equals 210. Moreover, while in the present example the IPF of a sunscreen was determined, the method may also be used to evaluate the IPF's of individual components of the sunscreen preparation.

Furthermore, while it is preferable that a UV source is used which emits both MUV and UVB radiation, a source emitting only UVA or UVB radiation can be used in a method of the invention.

If desired, increasing dosages of an amount of UV which is known not to suppress the immune response of the skin to the nickel may be used to determine the minimum dosage of UV which causes suppression of the immune response in the presence of the sunscreen. Accordingly, in this instance, it is not necessary to determine the MID and an IPF can be calculated using the dosage known not to cause immunosuppression of the skin.

EXAMPLE 2

A method for determining whether a cosmetic cream or other preparation causes suppression or enhancement of the immune response of the skin of a human being when the substance is applied to the skin is described below.

A 1 $cm^2$ test area of the skin of the mid-back of an individual is coated with a 2 $mg/cm^2$ amount of the substance for a period of 3 hours on each of five consecutive days.

After removal of the substance on the final day a nickel patch dosed with 0.5% nickel sulphate is applied to the test area. A further nickel patch containing the same dosage is applied to an area of the skin of the upper back as a positive control.

At the end of a 48 hour period the nickel patches are removed and the immune response of the skin to the nickel is assessed at the test area and the positive control after a further 24 hour period using the clinical scoring method used in Example 1.

In order to evaluate whether the substance suppressed the cutaneous immunity of the skin the clinical score for the test area is compared to the clinical score for the positive control. As will be appreciated, suppression of the immune response is indicated if the clinical score for the test area is lower than the clinical score for the positive control while enhancement of the immune response is indicated if the clinical score for the test area is higher than the clinical score for the positive control.

INDUSTRIAL APPLICABILITY

The method of the invention finds application by manufacturers in the development of preparations for topical application to the skin of persons. In particular, the method enables a manufacturer to determine whether a given preparation or ingredient for a preparation has any deleterious effects on the immune response of the skin or alternatively, whether the substance is able to protect the immune response from UV radiation. Once the effect on the immune response is known, the manufacturer can then modify the preparation or select other ingredients to ameliorate any adverse effect or improve the protection of the immune response provided by the substance.

In addition, the invention finds application in research into cutaneous carcinogenesis resulting from exposure to ultraviolet radiation or otherwise. The information provided by the method also finds use in the provision of information useful in the marketing of preparations, whether newly developed or previously known.

Although the present invention has been described hereinbefore with reference to several preferred methods, numerous variations and modifications are possible without departing from the scope of the invention which is defined in the following claims.

LIST OF REFERENCES CITED:

1. Noonan E P, de Fabo E C, Kripke M L. Suppression of Contact Hypersensitivity to UV Radiation and its Relationship to UV Induced Suppression of Tumour Immunity. Photochem Photobiol 1981; 34:683–689.

2. Hersey P, Hasic E, Edwards A, Bradley M, Haran G, McCarthy W H. Immunological Effects of Solarium Exposure. Lancet 1983; 545–548.

3. Ullrich S E, Azizi E, Kripke M L. Suppression of the Induction of Delayed-Type Hypersensitivity Reactions in Mice by a Single Exposure to Ultraviolet Radiation. Photochem Photobiol 1986; 6:633–638.

4. Cestari T F, Kripke M L, Baptista P L, Bakos L, Bucana C D. Ultraviolet Radiation Decreases the Granulomatous Response to Lepromin in Humans. J Invest Dermatol 1995; 103:8–13.

5. Cooper K D, Oberhelman L, Hamilton T A, Baadsgaard O, Terhune M, LeVee G et al. UV Exposure Reduces Immunisation Rates and Promotes Tolerance to Epicutaneous Antigens in Humans: Relationship to Dose, CD1a-DR+ Epidermal Macrophage Induction, and Langerhans Cell Depletion. Proc Natl Acad Sci 1992; 89:8497–8501.

6. London L J, Farmery S M, Will E J, Davison P M, Lodge J P A. Risk of Neoplasia in Renal Transplant Recipients. Lancet 1995: 346;403–406.

7. Espana A, Redondo P, Fernandez A L, Zabala M, Herreros J. Llorens R et al. Skin Cancer in Heart Transplant Patients. J Am Acad Dermatol 1995; 32:458–466.

8. Freeman S E, Ley R D, Ley K D. Sunscreen Protection Against UV-Induced Pyrimidine Dimers of DNA in Human Skin in situ. Photodermatol 1988, 5:243–247.

9. Thompson S C, Jolley D, Marks R. Reduction of Solar Keratoses by Regular Sunscreen Use. N Engl J Med 1993; 329:1147–51.

10. Naylor M F, Boyd A, Smith D W, Cameron G S, Hubbard D, Neldner K H. High Sun Protection Factor Sunscreens in the Suppression of Actinic Neoplasia. Arch Dermatol 1995; 131:170–175.

11. Kilgman L E, Akin P J, Kligman A M. Sunscreens Prevent Ultraviolet Carcinogenesis. J Am Acad Dermatol 1980; 3:30–35.

12. Whitmore S E, Morison W L. Prevention of UVB-Induced Immunosuppression in Humans by a High Sun Protection Factor Sunscreen. Arch Dermatol 1995; 131:1128–1133.

13. Bestak R, Barnetson R StC, Nearn M R, Halliday G M. Sunscreen Protection of Contact Hypersensitivity Responses from Chronic Solar-Simulated Ultraviolet Irradiation Correlates with the Absorption Spectrum of the Sunscreen. J Invest Dermatol 1995; 105:345–351.

14. Peltonen L. Nickel Sensitivity in the General Population. Contact Dermatitis 1979; 5:27–32.

15. Meijer C, Bredberg M, Fischer T, Widstrom L. Ear Piercing, and Nickel and Cobalt Sensitisation, in 520 Young Swedish Men Doing Compulsory Military Service. Contact Dermatitis. 1995; 32:147–149.

16. Hemon A A, Friedmann P S. Studies on the Reproducibility of Allergic Contact Dermatitis. Br J Deratol 1996; 134:208–214.

We claim:

1. A method of evaluating an effect of a substance when applied to mammalian skin, comprising the steps of:
   (i) assessing an immune response of the skin of at least one mammal to an antigen, to which the mammal has been sensitised, in order to obtain data;
   (ii) applying the substance to the skin;
   (iii) assessing the immune response of the skin to the antigen following the application of the substance to obtain further data; and
   (iv) using the data obtained in steps (i) and (iii) to determine information to evaluate the effect of the substance.

2. A method according to claim 1 wherein the method further comprises the step of substantially removing the substance from the skin prior to step (iii).

3. A method according to claim 1 wherein a batch of the substance is to be evaluated and a sample from the batch or a sample of the substance obtained separately from the batch is used in the evaluation.

4. A method according to claim 1, wherein the evaluating comprises determining whether the substance suppresses, enhances or protects the immune response of the skin to the antigen.

5. A method according to claim 1 wherein the substance is a sunscreen, cosmetic or pharmaceutical preparation.

6. A method according to claim 4, wherein step (ii) further comprises exposing the skin to ultraviolet radiation and the evaluating comprises determining the level of protection provided by the substance to the immune response of the skin from the ultraviolet radiation.

7. A method according to claim 6 wherein the skin is exposed to a selected range of dosages of the ultraviolet radiation that includes dosages able to suppress the immune response of the skin to the antigen in the absence of the application of the substance to the skin, and step (iii) involves assessing the immune response of the skin at each of the dosages.

8. A method according to claim 7 wherein each of the dosages of the ultraviolet radiation are applied to the skin over a predetermined number of days.

9. A method according to claim 7 wherein step (i) further comprises exposing the skin to an initial range of dosages of ultraviolet radiation and the immune response of the skin is assessed at each of those dosages, and wherein at least one of the initial dosages suppresses the immune response.

10. A method according to claim 9 wherein the initial and the selected range of dosages of ultraviolet radiation are applied to the skin over a predetermined number of days, respectively.

11. A method according to claim 10 wherein obtaining the data in steps (i) and (iii) comprises determining minimum dosages of the ultraviolet radiation that suppress the immune response of the skin to the antigen.

12. A method according to claim 1, wherein the antigen is selected from the group consisting of a metal and a polypeptide.

13. A method according to claim 1, wherein the antigen is nickel or chrome.

14. A method according to claim 1, wherein the antigen is applied to the surface of the skin or is injected into the skin to evaluate the immune response of the skin in steps (i) and (iii).

* * * * *